(12) United States Patent
Dalton

(10) Patent No.: US 6,979,334 B2
(45) Date of Patent: Dec. 27, 2005

(54) BONE FIXATION ASSEMBLY AND METHOD OF SECUREMENT

(75) Inventor: Brain E. Dalton, Erie, PA (US)

(73) Assignee: Aesculap, Inc., Center Valley, PA (US)

( * ) Notice: Subject to any disclaimer, the term of this patent is extended or adjusted under 35 U.S.C. 154(b) by 0 days.

(21) Appl. No.: 10/815,160

(22) Filed: Mar. 31, 2004

(65) Prior Publication Data

US 2005/0010219 A1   Jan. 13, 2005

Related U.S. Application Data

(63) Continuation-in-part of application No. 10/731,625, filed on Dec. 9, 2003, which is a continuation-in-part of application No. 10/615,196, filed on Jul. 7, 2003.

(51) Int. Cl.$^7$ .............................................. A61B 17/58
(52) U.S. Cl. .............................. 606/61; 606/69; 606/73
(58) Field of Search ...................... 606/61, 66, 69–73, 606/67

(56) References Cited

U.S. PATENT DOCUMENTS

| | | |
|---|---|---|
| 4,463,753 A | 8/1984 | Gustilo |
| 4,484,570 A | 11/1984 | Sutter et al. |
| 5,129,899 A * | 7/1992 | Small et al. ................... 606/61 |
| 5,147,363 A | 9/1992 | Härle |
| 5,486,176 A | 1/1996 | Hildebrand et al. |
| 5,520,690 A | 5/1996 | Errico et al. |
| 5,531,746 A | 7/1996 | Errico et al. |
| 5,540,690 A | 7/1996 | Miller et al. |
| 5,607,426 A | 3/1997 | Ralph et al. |
| 5,620,443 A | 4/1997 | Gertzbein et al. |
| 5,669,911 A | 9/1997 | Errico et al. |
| 5,735,853 A | 4/1998 | Olerud |
| 5,749,916 A | 5/1998 | Richelsoph |
| 5,797,911 A | 8/1998 | Sherman et al. |
| 5,800,433 A | 9/1998 | Benzel et al. |
| 5,863,293 A | 1/1999 | Richelsoph |
| 5,876,402 A | 3/1999 | Errico et al. |
| 5,879,350 A | 3/1999 | Sherman et al. |
| 5,885,286 A | 3/1999 | Sherman et al. |
| 5,954,635 A | 9/1999 | Foley et al. |
| 5,954,722 A | 9/1999 | Bono |
| 5,964,760 A | 10/1999 | Richelsoph |
| 5,976,187 A | 11/1999 | Richelsoph |
| 6,022,350 A | 2/2000 | Ganem |
| 6,030,389 A | 2/2000 | Wagner et al. |
| 6,033,406 A | 3/2000 | Mathews |
| 6,053,917 A | 4/2000 | Sherman et al. |
| 6,074,391 A | 6/2000 | Metz-Stavenhagen et al. |

(Continued)

*Primary Examiner*—Glenn K. Dawson
*Assistant Examiner*—D. Jacob Davis
(74) *Attorney, Agent, or Firm*—RatnerPrestia

(57) ABSTRACT

A bone plate is provided for fixation of spaced vertebra. The bone plate has at least one through passage for securing the plate to bone with a bone fixation screw. The threaded shaft of a bone fixation screw is inserted through a bushing located in the through passage of the bone plate and the screw is thereby threadably secured to the underlying bone and the bushing is then compressed inward against the head of the screw with cams that are actuated by rotating the bushing in the through passage whereby the screw is locked relative to the bone plate. The bushing is not only compressed inwardly against the head of the screw but is also compressed downwardly by the cams into a seat to clamp separate elements of the bone plate together.

10 Claims, 5 Drawing Sheets

U.S. PATENT DOCUMENTS

| | | | |
|---|---|---|---|
| 6,083,225 A | 7/2000 | Winslow et al. |
| 6,096,038 A | 8/2000 | Michelson |
| 6,132,432 A | 10/2000 | Richelsoph |
| 6,146,386 A | 11/2000 | Blackman et al. |
| 6,152,871 A | 11/2000 | Foley et al. |
| 6,159,179 A | 12/2000 | Simonson |
| 6,162,170 A | 12/2000 | Foley et al. |
| 6,171,311 B1 | 1/2001 | Richelsoph |
| 6,197,033 B1 | 3/2001 | Haid, Jr. et al. |
| 6,200,322 B1 | 3/2001 | Branch et al. |
| 6,206,822 B1 | 3/2001 | Foley et al. |
| 6,217,509 B1 | 4/2001 | Foley et al. |
| 6,235,033 B1 * | 5/2001 | Brace et al. ............... 606/61 |
| 6,261,291 B1 | 7/2001 | Talaber et al. |
| 6,280,442 B1 | 8/2001 | Barker et al. |
| 6,280,445 B1 | 8/2001 | Morrison et al. |
| 6,287,311 B1 | 9/2001 | Sherman et al. |
| 6,290,703 B1 | 9/2001 | Ganem |
| 6,299,616 B1 | 10/2001 | Beger |
| 6,328,738 B1 | 12/2001 | Suddaby |
| 6,328,740 B1 | 12/2001 | Richelsoph |
| 6,328,741 B1 | 12/2001 | Richelsoph |
| 6,331,179 B1 | 12/2001 | Freid et al. |
| RE37,665 E | 4/2002 | Ralph et al. |
| 6,402,752 B2 | 6/2002 | Schäffler-Wachter et al. |
| 6,402,756 B1 | 6/2002 | Ralph et al. |
| 6,428,542 B1 | 8/2002 | Michelson |
| 6,451,021 B1 | 9/2002 | Ralph et al. |
| 6,514,260 B1 | 2/2003 | Zdeblick et al. |
| 6,520,907 B1 | 2/2003 | Foley et al. |
| 6,527,776 B1 | 3/2003 | Michelson |
| 6,530,929 B1 | 3/2003 | Justis et al. |
| 6,533,786 B1 | 3/2003 | Needham et al. |
| 6,562,046 B2 | 5/2003 | Sasso |
| 6,565,565 B1 | 5/2003 | Yuan et al. |
| 6,575,899 B1 | 6/2003 | Foley et al. |
| 6,575,975 B2 | 6/2003 | Brace et al. |
| 6,599,290 B2 | 7/2003 | Bailey et al. |
| 6,602,255 B1 | 8/2003 | Campbell et al. |
| 6,623,485 B2 | 9/2003 | Doubler et al. |
| 6,645,207 B2 | 11/2003 | Dixon et al. |
| 6,663,616 B1 | 12/2003 | Roth et al. |
| 6,682,534 B2 | 1/2004 | Patel et al. |
| 6,695,772 B1 | 2/2004 | Bon et al. |
| 6,695,846 B2 | 2/2004 | Richelsoph et al. |
| 6,712,818 B1 | 3/2004 | Michelson |
| 6,712,819 B2 | 3/2004 | Zucherman et al. |
| 6,780,185 B2 | 8/2004 | Frei et al. |
| 6,780,186 B2 | 8/2004 | Errico et al. |
| 2001/0034521 A1 | 10/2001 | Bailey et al. |
| 2001/0037111 A1 | 11/2001 | Dixon et al. |
| 2002/0161368 A1 | 10/2002 | Foley et al. |
| 2002/0183754 A1 | 12/2002 | Michelson |
| 2003/0045875 A1 | 3/2003 | Bertranou et al. |
| 2003/0060826 A1 | 3/2003 | Foley et al. |
| 2003/0073996 A1 | 4/2003 | Doubler et al. |
| 2003/0149431 A1 | 8/2003 | Varleur |
| 2003/0208203 A1 | 8/2003 | Lim et al. |
| 2003/0216735 A1 | 11/2003 | Altarac et al. |
| 2004/0039384 A1 | 2/2004 | Boehm, Jr. et al. |
| 2004/0127897 A1 | 7/2004 | Freid et al. |
| 2004/0133207 A1 | 7/2004 | Abdou |

* cited by examiner

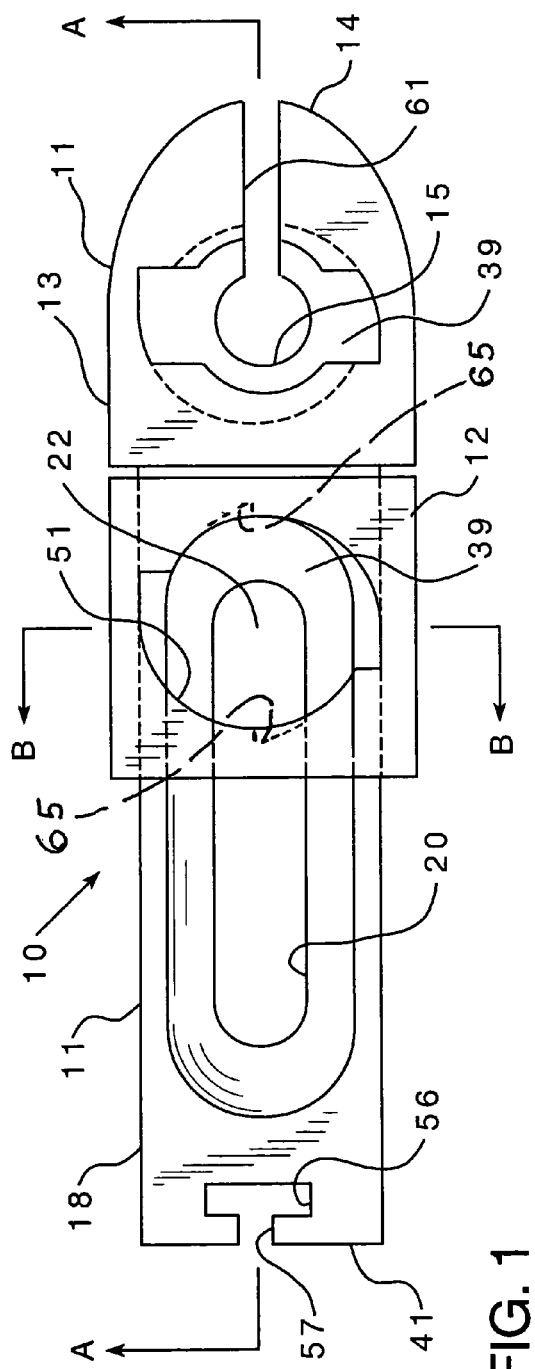
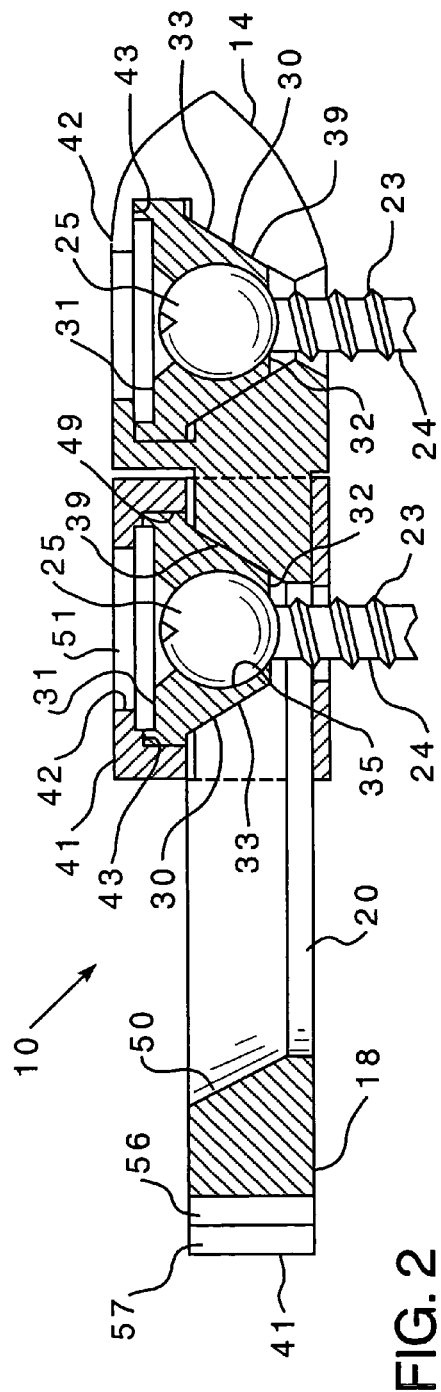
FIG. 1
FIG. 2

BONE FIXATION ASSEMBLY AND METHOD OF SECUREMENT

CROSS-REFERENCE

This is a continuation-in-part of U.S. application Ser. No. 10/731,625, filed Dec. 9, 2003, for BONE FIXATION ASSEMBLY AND METHOD OF SECUREMENT, which is a continuation-in-part of U.S. application Ser. No. 10/615,196, filed Jul. 7, 2003, for SPINAL STABILIZATION IMPLANT AND METHOD OF APPLICATION.

FIELD OF THE INVENTION

The present invention relates generally to spinal fixation systems. More particularly, the present invention pertains to a spinal plate assembly which includes a mechanism for fixably attaching and locking bone fixation screws to the plate at desired angles and for simultaneously locking otherwise adjustable portions of the plate together.

BACKGROUND OF THE INVENTION

Spinal surgery on the lumbar and thoracic spines have classically been open operations, meaning that the instrumentation used is placed through an incision that exposes all of the spine to be instrumented, as well as a portion of spine above and below the area to be instrumented due to the need for proper visualization. This extensive exposure disrupts a considerable amount of tissue, particularly the lumbar paraspinal musculature which needs to be stripped off the vertebra bones for exposure. This stripping leads to muscle damage directly caused by either electrical cautery or manual cutting or indirectly by interruption of vascular supply to the muscle due to coagulation or cutting of vessels, and caused also by embarrassment of the vascular supply during the course of surgery due to compression by retractors on the muscle which are required to maintain exposure. In addition, spinal implants can impact upon the facet joints of the spine, particularly the upper most pair of pedicle screws, which can cause pain or dysfunction of the involved joint. This is due in part to the fact that the pedicle screw systems are designed to give stability without being made to respect normal anatomy. In other words, the spine is forced to fit the metal, instead of fitting the metal to the spine.

The present day surgical approach therefore has added to patient morbidity due to the extent of the surgical exposure, tissue damage done primarily to the posterior longitudinal musculature of the spine during the exposure, blood loss and risk of infection. Large open operations also tend to be the cause of significant postoperative pain and disability. Accordingly, these issues lead to longer hospital stays, higher postoperative complications, such as phlebitis and pneumonia brought on by immobility, and greater consumption of postoperative medications with their resultant side affects. In addition, the paraspinal muscle tissue damage has been implicated in the genesis of postoperative lumbar mechanical dysfunction and stiffness, leading to postoperative pain syndromes or failed back syndrome. Also, interference by metal implants of the normal function of the rostral facet joints has been implicated in the early degeneration of these joints, as well as pain and disability, all which could lead to other more involved surgeries.

It is a principal object of the present invention to provide a system, including the spinal implant and a delivery system for applying the implant which allows for minimally invasive placement of the spinal implant, thereby reducing the undesired aforedescribed disadvantages of the prior art surgical procedures.

Another object of the present invention is to provide a bone fixation assembly which provides polyaxial locking of the screws to the plate and simultaneously, as required, locking of otherwise adjustable portions of the bone plate together for use in the spinal stabilization application method disclosed in corresponding U.S. application Ser. No. 10/615,196.

SUMMARY OF THE INVENTION

The bone fixation assembly of the present invention includes a bone plate having through passages for inserting the threaded shafts of fastening screws to secure the plate to underlying bone. The threaded screw shaft is inserted through a bushing located in the through passage of the bone plate and threadably secured into the underlying bone. The bushing is configured and dimensioned whereby it is compressed against the head of the screw with cams which are actuated by rotating the bushing in the through passage of the plate whereby the screw is locked relative to the bone plate. The bushing may also simultaneously be compressed downwardly into a seat in order to clamp separate elements of an otherwise adjustable bone plate together to securely lock them.

The head of the bone fixation screw has substantially frusto-spherical shaped side surfaces and the bushing in which the screw head is received has an interior surface which defines a socket bore that extends through upper and lower surfaces of the bushing and is configured and dimensioned for polyaxial rotation of the screw head therein. Exterior surfaces of the bushing are configured and dimensioned for limited axial rotation within the through passage of the fixation device or bone plate. At least one slot is located in the side wall of the bushing for allowing inward compression of the bushing bore against the screw head. A cam mechanism is disposed between the through passage of the plate and the bushing and is configured and dimensioned for inwardly compressing the bushing upon axial rotation of the bushing in the through passage whereby the bore is compressed against the screw head for locking the screw at a desired attitude relative to the fixation device or plate.

The bushing socket bore is provided with a substantially frusto-spherical shape with a central longitudinal axis to provide initial polyaxial rotation of the screw head therein. One slot within the bushing may extend from the upper surface of the bushing on through the lower surface of the bushing whereby the bushing is generally C-shaped and may thereby be more readily inwardly compressed with a cam mechanism.

In a preferred configuration the through passage of the fixation device is provided with an inverted frusto-conical seat and the exterior surface of the bushing is provided with a mating inverted frusto-conical base configured and dimensioned for seating in this seat. The seat and base are coaxial with the central axis of the bushing and through passage. The cam mechanism may take on different configurations. For example, the cam mechanism may be a threaded engagement of thread cam ramps or the use of other types of cam ramps. For example, the cam mechanism may be comprised of annularly spaced upwardly extending ramp cams on the upper surface of the bushing and inwardly extending overhangs are provided on the through passage above the upper surface of the cams or bushing and this overhang is provided with downwardly facing cam following surfaces that are configured and dimensioned for engaging the ramp cams on the top of the bushing when the bushing is axially rotated in its seat. This rotation causes the bushing to be driven downwardly into its inverted frusto-conical seat by the ramp cams to thereby inwardly compress the bushing bore against the screw head. The cams and cam followers surfaces may also be provided for ridges to prevent back-out of the cams.

The bone fixation assembly of the present invention is intended to be used independently or in supplement to the bone fixation assembly and method of application described in the inventor's related application previously identified. The bone fixation device of this embodiment is adjustable and is provided with a first screw receiving socket element at a distal end of the plate assembly which is configured with a screw shank passage and a screw head seat for attachment to bone with the aid of a bone fixation screw. An elongate arm extends proximally from this first socket element and has an elongate through slot therealong. A second screw receiving socket element is provided and includes the afore-described through passage containing the bushing and cam mechanism. This second screw receiving socket element is slidably received over the arm with the socket bore thereof aligned over the slot for receiving the shank of a fixation screw therethrough for attachment to bone. The bushing seat includes portions of the through slot whereby the second socket element is clamped and locked to the arm when the bushing is pressed downwardly into the seat by the cam mechanism.

BRIEF DESCRIPTION OF THE DRAWINGS

Other objects and advantages appear hereinafter in the following description and claims. The accompanying drawings show, for the purpose of exemplification, without limiting the invention or appended claims, certain practical embodiments of the present invention wherein:

FIG. 1 is a plan view of the bone fixation assembly of the present invention without inclusion of the screw head bushings;

FIG. 2 is a view in front elevation and in vertical mid cross section of the bone fixation assembly shown in FIG. 1 as seen along section line A—A with inclusion of the screw head bushings;

DETAILED DESCRIPTION OF PREFERRED EMBODIMENTS

Figure 3:
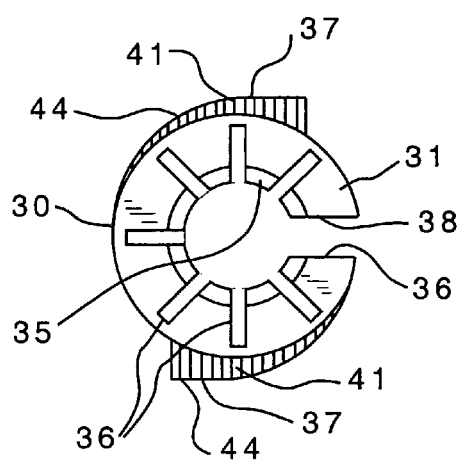
FIG. 3 is a top view of the C-shaped compression bushing utilized in the assembly of FIGS. 1 and 2.
Figure 4:
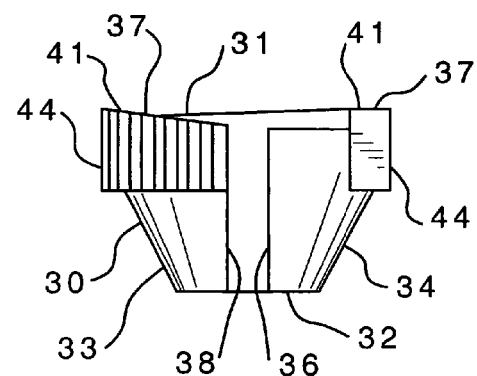
FIG. 4 is a view in right side elevation of the bushing shown in FIG. 3.
Figure 5:
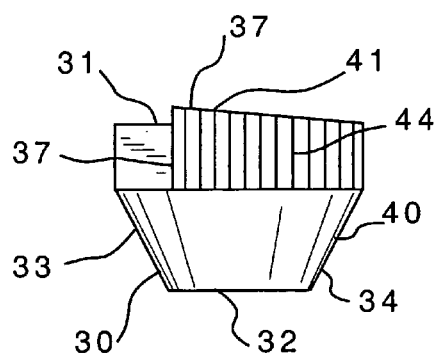
FIG. 5 is a view in front elevation of the bushing shown in FIG. 3.
Figure 6:
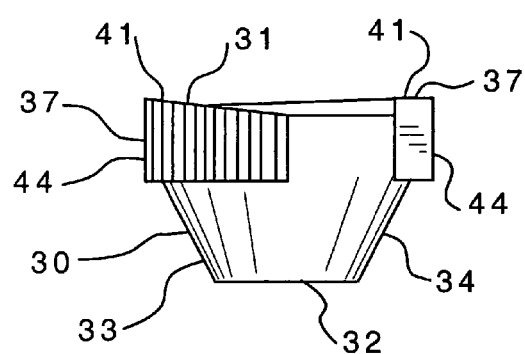
FIG. 6 is a view in left side elevation of the bushing shown in FIG. 3.

Referring first to FIGS. 1 and 2, the bone fixation assembly 10 of the present invention is provided for stabilization of the spine and is an improved modification of the implant plate assembly shown and described in the inventor's aforementioned copending application for use in the inventive procedure therein described for minimum invasive surgical implantation of a plate assembly for fixation of the spine. The assembly 10 is comprised of two separate portions, a first portion 11 and a second portion 12 which are adjustably assembled together. The first portion 11 includes a first receiving socket element 13 at the distal end 14 of assembly 10. This first screw receiving socket element 13 is configured with a screw shank through passage 15 for attachment of element 13 to vertebra bone with the aid of a bone fixation screw 23 as seen in FIG. 2. The plan view of FIG. 1 does not include the bone fixation screws and other interior parts which are included in FIG. 2 in order to provide an exposed view of the screw shank through passage interiors of elements 12 and 13.

First portion 11 further includes an elongate arm 18 extending proximally from the first socket element 13. Elongate arm 18 is provided with an elongate through slot 20 therealong. The second portion 12 of assembly 10 comprises a second screw receiving socket element which is also configured with a screw shank through passage 22. Second screw receiving socket element 12 is slidably received over arm 18 with its through passage 22 centered over and aligned over slot 20 for receiving the shank 24 of a fixation screw 23 therethrough for attachment to underlying vertebra bone. The bone fixation or fastening screws 23 have threaded shanks or shafts 24 for insertion through the respective through passages 15 and 22 and they also are provided with heads 25 which have substantially frusto-spherical shaped side surfaces.

Bushings 30 are provided for each socket element 12 and 13 to receive the respective screw heads 25. These bushings have upper surfaces 31 and lower surfaces 32 and a side wall 33. The detail of these bushings 30 are best illustrated in FIGS. 3, 4, 5 and 6.

The side wall 33 of each bushing 30 is provided with an exterior surface 34 which is configured in dimension for axial rotation within the respective through passages 15 and 22 of screw socket receiving elements 12 and 13. The interior surface 35 of bushings 30 defines a socket bore that extends through the upper and lower surfaces 31 and 32 and is configured and dimensioned for polyaxial rotation of screw head 25 therein. Plural slots 36 are provided in the side wall 33 for allowing inward compression of bore 35 against screw head 25. A cam mechanism 37 is disposed between through passages 15 and 22 and bushings 30 and this cam mechanism 37 is configured and dimensioned for inwardly compressing bushing 30 upon axial rotation of each bushing 30 in its respective through passage 15 and 22 whereby the bore 35 of bushing 30 is compressed against its respective screw head 25 received therein for locking the screw 23 at a desired attitude relative to the fixation plate or device 10. The bushing socket bore 35 has a substantially frusto-spherical shape to compliment the screw heads 25 and has its central longitudinal axis perpendicular to upper and lower surfaces 31 and 32. Also, one of the slots 36 in the form of slot 38 for bushing 30 extends fully through side wall 33 from the upper surface 31 through the lower surface 32. This provides a C-shape to bushing 30 and permits greater compression of the bushing.

The bottom portion of each through passage 15 and 22 is provided with an inverted frusto-conical seat 39 and the exterior surface 33 of the bushings 30 are provided with a mating inverted frusto-conical base 40 configured and dimensioned for seating respectively in said seats 39. Seat 39 and base 40 are coaxial with the central axis of the bushing bore 35.

The cam mechanism 37 includes annularly spaced upwardly extending ramp cams 41 on the upper surface 31 of bushing 30 and inwardly extending overhangs 42 on the through passages 15 and 22 which are positioned above the upper surface 31 of cams 30. Overhangs 42 are provided with downwardly facing cam following surfaces 43 configured and dimensioned for engaging the cam ramps 41 when bushing 30 is axially rotated in either through passage 15 or 22 whereby the bushing 30 is driven downwardly into seat 39 by the ramp cams 41 to thereby inwardly compress bushing bore 35 against a screw head 25.

This cam mechanism 37 further includes radially extending ramp cams 44 on the exterior surface 33 of bushing 30 and these additional ramp cams are dimensioned and configured for also compressing socket bore 35 inwardly when bushing 30 is axially rotated in through passage 15 or 22 due to the manner in which the side walls of through passages 15 and 22 are configured. As illustrated in FIGS. 3 through 6, the ramp cams 41 and 44 are provided with ridges to prevent rotary back off of the bushing 30 after it has been secured within respective through passage 15 or 22.

The bushing seat 39 for second socket receiving element 12 includes sloped mating portions 50 of through slot 22 for arm 18 whereby second socket receiving element 12 is firmly clamped to arm 18 when bushing 30 is pressed downwardly into through passage 22 onto seat 39 by the cam mechanism 37. Bushing 30 not only securely locks screw head 35 at a desired attitude, but simultaneously also securely locks second screw socket receiving element 12 to arm 18 at the position desired. This locking capability is schematically illustrated step by step in FIGS. 7 through 10. The schematic illustrations are generally intended to show a cross section through the fixation device 10 of FIG. 1 as seen along section line B—B. However, for the purposes of simplification of illustration, the exact orientation of the bushings 30 relative to the device 10 is not identical to that illustrated in FIGS. 1 and 2.

Figure 7:
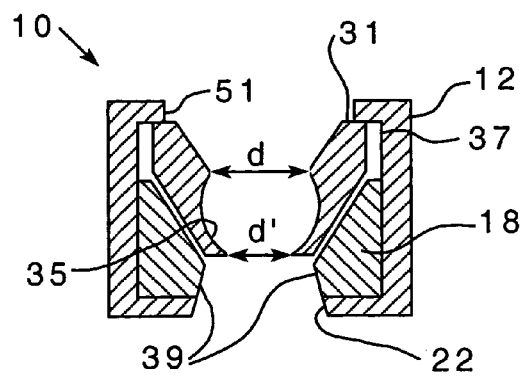
FIGS. 7, 8, 9 and 10 are sequential schematic representations illustrating the operation of the locking mechanism for the assembly shown in FIG. 1 as seen along a mid cross section.

FIG. 7 illustrates the ready position as the parts are initially assembled ready for application. The bushing 30 has been inserted into socket receiving element 12. This is accomplished at the manufacturing stage by compressing the C-shaped bushing 30 sufficiently that it will pass through upper passage 51 of element 12. After insertion, bushing 30 is released from compression and the outer edges of upper surface 31 expand radially outward whereby they underlie overhangs 42. This prevents bushing 30 from accidentally dislodging from element 12.

Figure 8:
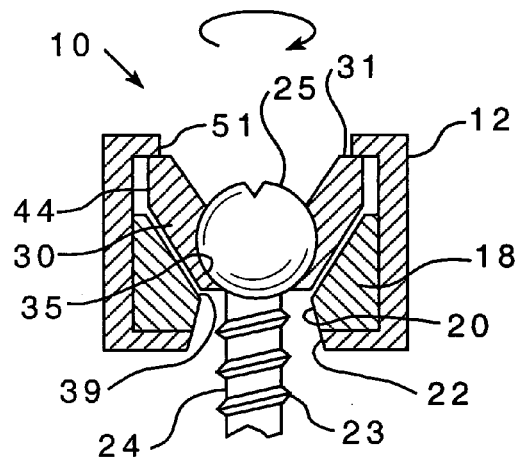

Note that in this ready position the upper lip diameter d of bushing 30 is slightly less that the diameter of screw head 25 and that the lower lip diameter d' is less than the diameter screw head 25. Accordingly, in the second step of the process, screw shank 24 is inserted through the bushing bore 35 and on through passage 22 of element 12 and the head 25 is then forcibly radially expands bushing 30 and the head 25 snaps down into the bushing 30 where it is retained in bushing bore 35, the diameter d' being too small for forcible passage of the head 25 therethrough. This step is accomplished by screwing threaded shank 24 of screw 23 into underlying vertebra until head 25 snaps downwardly into bushing 30 as illustrated in FIG. 8. To accomplish this, screw 25 is of course rotated clockwise as indicated by the arrow.

Figure 9:
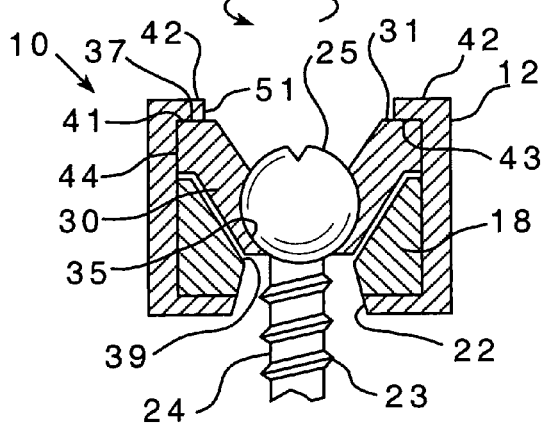

The next step is then schematically illustrated in FIG. 9 wherein bushing 30 is rotated counterclockwise as indicated by the arrow at the top of FIG. 9. This is accomplished by an outer 8 toothed Phillips' type driver which engages slots 36 and which has a hollow shaft interior whereby it is arranged or coaxially received over a central hex-driver for driving the screws 23. This combination of screwdrivers is not shown but can be easily visualized and permits the surgeon to retain screw head 25 stationary while rotating the bushing 30 counterclockwise.

Figure 10:
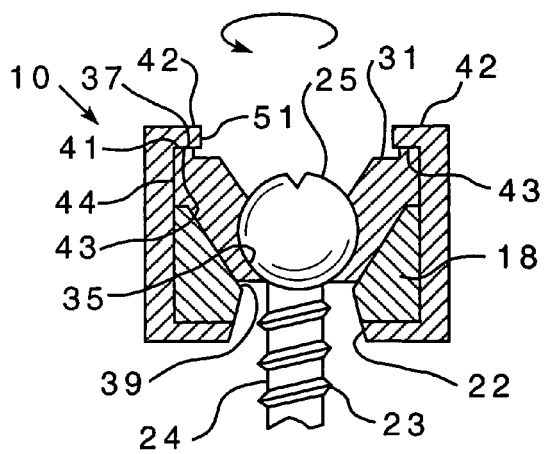

Due to the cam mechanism 37, which provides upwardly protruding cam ramps 41 and radially protruding ramp cams 44, this counterclockwise turn of bushing 30 causes the radially extending ramp cams 44 to compress bushing 30 and corresponding bore 35 inwardly and to thereby firmly engage screw head 25 and continuing counterclockwise turning of bushing 30 also causes bushing 30 to drive downward into seat 39 as further illustrated in FIG. 10 thereby locking screw head 25 in its trajectory relative to fixation device 10 due to the action of ramp cams 41 acting against follower cam surfaces 43 of overhangs 42. This securely locks arm 18 relative to socket receiving element 12 and further securely locks screw 23 at the given attitude to the entire device 10.

As is best illustrated in FIG. 2, the follower cams 43 of overhangs 42 may be provided with downwardly extending ramp cams as illustrated to compliment the upwardly extending ramp cams 41 of bushings 30. The follower cam surfaces 41 and also the radially facing cam surfaces 49 of element 12 may be provided with complimentary ridges to prevent rotary back-out of the bushing 30 after it is locked into position.

Also, with reference to FIGS. 1 and 2, cam surfaces 49 of receiving element 12 are provided with locking recesses 65. Bushing 30 only requires a one quarter counterclockwise turn to fully compress the bushing against screw head 25. Accordingly, the recesses 65 are provided just past the point of maximum compression for bushing 30. Two of these locking recesses are provided on opposite sides of element 12, one for each radially protruding ramp cam 44. Once bushing 30 has been fully compressed by the quarter counterclockwise turn, the bushing 30 is allowed very slight expansion whereby the corners of radially extending ramp cams 44 snap into the locking recesses 65. This prevents the bushing 30 from turning clockwise and releasing itself and it also provides a mechanical feedback to the surgeon that the bushing 30 is fully locked. The incorporation of locking recesses 65 permits the elimination of the requirement of ridges on the ramp cams 41 and 44. This arrangement also permits the bushing 30 to be turned counterclockwise against maximal torque beyond the quarter turn back to the resting point or starting point of the bushing through another quarter turn which permits release of the bushing 30 and screw head 25. In this manner, the surgeon may elect to adjust the implant even after the bushing 30 has been locked.

The through slot 57 and retainer slot 56 on the proximal end 41 of bone fixation device 10 is provided for coupling the device to an insertion gun as described and illustrated in the inventor's aforesaid copending application for minimum invasive surgical application of the device of the present invention. For more information in this regard, one should refer to this document and it is accordingly incorporated herein by reference.

An alternative embodiment of the cam mechanism 37 is illustrated in FIGS. 11 through 15. In this embodiment, the C-shaped bushing 30 is again provided with an inverted frustoconical base portion 33 for mating and seating in the inverted frustoconical seat 39 of through passage 15 in socket element 13. However, in this embodiment, the cam mechanism 37 is provided in the form of thread cam ramps by male threads 45 on the inverted frustoconical surface 33 of bushing 30 and mating female threads 46 on the inverted frustoconical mating seat of through passage 15.

Figure 13:
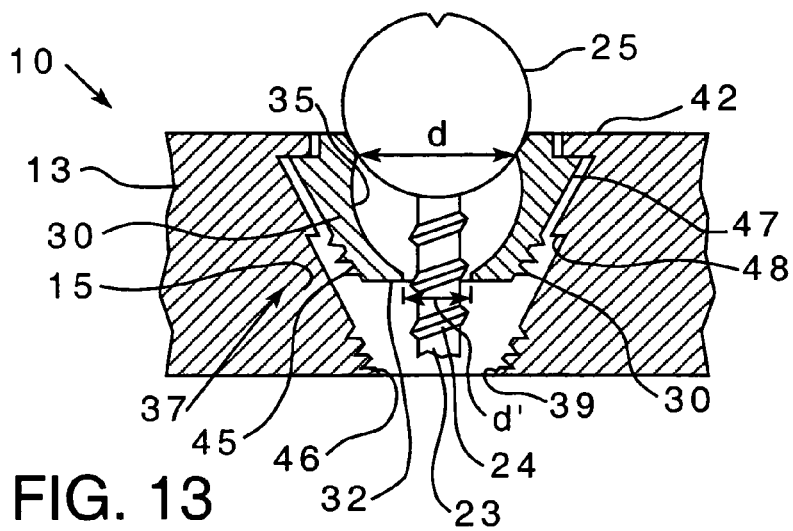
FIGS. 13, 14 and 15 are sequential schematic representations illustrating the operation of an alternative embodiment of the locking mechanism for the assembly shown in FIG. 1 as seen along section line B—B and incorporating the bushing shown in FIGS. 11 and 12.

FIG. 13 illustrates the initial conditions of installation wherein the screw 23 is being inserted into the bore 35 of bushing 30. Bushing 30 is retained in position in socket element 13 by means of overhangs 42 which overhang annular lip 47 of bushing 30, thereby preventing back out of bushing 30.

Figure 14:
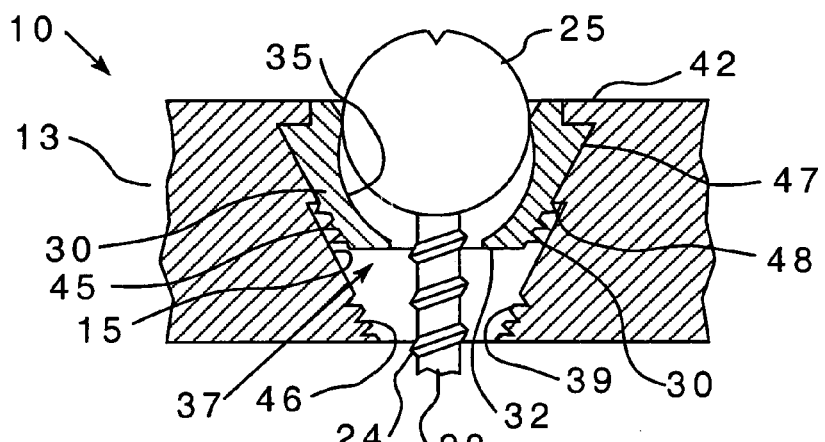

Once screw head 25 is forced downwardly as indicated by the arrow in FIG. 14, the C-shaped bushing 30 is spread and permits head 25 to enter and to be confined by the internal bore 35. The screw head 25 is rotated clockwise by an appropriate screwdriver until the shank portion 24 is fully engaged in underlying bone (not shown).

Figure 11:
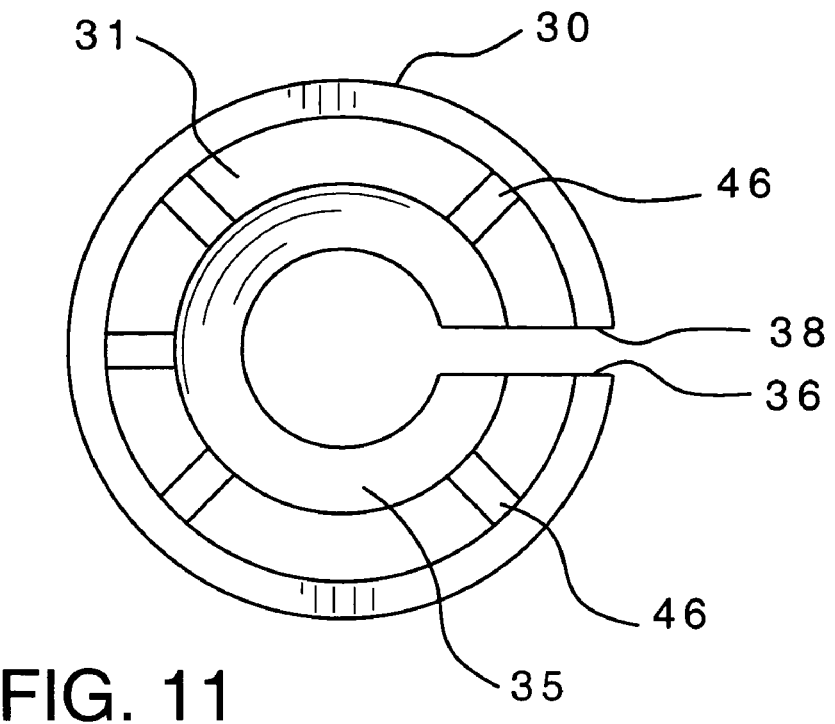
FIG. 11 is a top view of an alternative embodiment of the C-shaped compression bushing to be utilized in the assembly of FIGS. 1 and 2.
Figure 12:
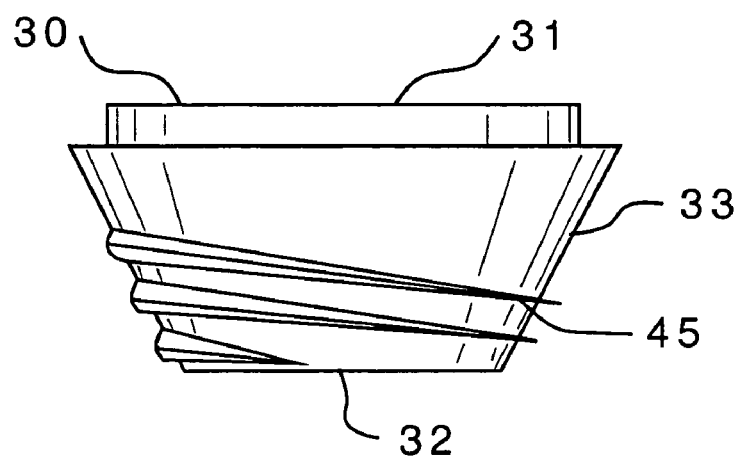
FIG. 12 is a view in front elevation of the bushing shown in FIG. 11.
Figure 15:
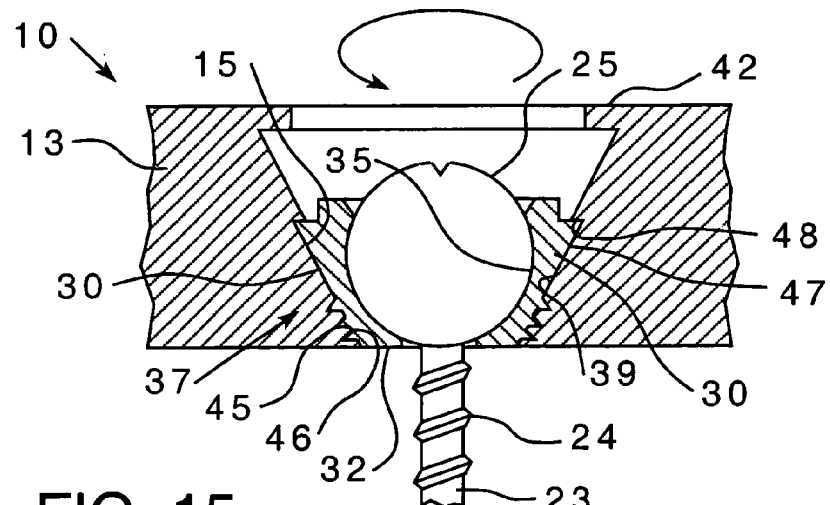

At this point, a special screwdriver is utilized to engage the drive recesses 46 in the top 31 of bushing 30, as is best illustrated in FIG. 11, and bushing 30 is thereby pushed downward and rotated counterclockwise as indicated by the arrow in FIG. 15. This causes the threads 45 and 46 of cam mechanism 37 to engage and thereby further compresses C-shaped bushing 30 inwardly and downwardly until the protruding annular lip 47 engages under the annular seat 48, whereby bushing 30 is engaged and prevented from backing out from its threaded engagement. This procedure securely locks the head 25 of screw 23 from further polyaxial rotation within the bore 35 of bushing 30.

I claimed:

1. A bone fixation assembly comprising:
   (a) a fixation device having a through passage;
   (b) a fastening screw having a threaded shaft for insertion through the through passage and threadable insertion into bone, and a head having substantially frustospherical shaped side surfaces;
   (c) a bushing having;
      (i) upper and lower surfaces;
      (ii) a side wall with an exterior surface configured and dimensioned for axial rotation within said through passage of the fixation device and an interior surface which defines a socket bore that extends through the upper and lower surfaces and is configured and dimensioned for polyaxial rotation of said screw head therein; and
      (iii) at least one slot located on the sidewall for allowing inward compression of said bore against said screw head; and
      (iv) an access passage in said upper surface dimensioned for receiving said screw head therethrough for access to said socket bore;
   cam means disposed on and integral with said bushing, said cam means disposed between said through passage and said bushing and configured and dimensioned for inwardly compressing said bushing upon axial rotation thereof in said through passage whereby said bore is compressed against said screw head for locking said screw at a desired attitude relative to said fixation device.

2. The bone fixation assembly of claim 1 wherein said bushing socket bore has a substantially frustospherical shape with a central longitudinal axis.

3. The bone fixation assembly of claim 2 wherein said socket bore extends through the central axis of said bushing and is perpendicular to the upper and lower surfaces.

4. The bone fixation assembly of claim 3 wherein one of said at least one slot is a slot extending fully through said side wall from the upper surface through the lower surface and said access passage is dimensioned for receiving said screw head therethrough with a snap fit by expanding said access passage.

5. The bone fixation assembly of claim 4 wherein a bottom portion of said through passage has an inverted frustoconical seat and said exterior surface of said bushing has a mating inverted frustoconical base configured and dimensioned for seating in said seat, said seat and said base coaxial with said central axis, said cam means comprised of annularly spaced upwardly extending ramp cams on said upper surface of said bushing and said access passage including inwardly extending overhangs on said through passage positioned above said upper surface and having downwardly facing cam following surfaces configured and dimensioned for engaging said ramp cams when said bushing is axially rotated in said through passage whereby said bushing is driven downwardly into said seat by said ramp cams to thereby inwardly compress said bushing bore against said screw head.

6. The bone fixation assembly of claim 5 wherein said cam means includes radially extending ramp cams on said exterior surface of said bushing dimensioned and configured for compressing said socket bore inwardly when said bushing is axially rotated in said through passage.

7. The bone fixation assembly of claim 6 wherein said cam means includes ridges on at least one of said cams.

8. The bone fixation assembly of claim 4 wherein a bottom portion of said through passage has an inverted frustoconical seat and said exterior surface of said bushing has a mating inverted frustoconical base configured and dimensioned for seating in said seat, said seat and said base coaxial with said central axis, said cam means comprised of a threaded engagement between said bottom portion of said through passage and said bushing base whereby when said bushing is rotated in said through passage seat said bushing is drawn into said seat and thereby inwardly compressed against said screw head.

9. The bone fixation assembly of claim 8 wherein said threaded engagement is configured with left hand threads.

10. The bone fixation assembly of claim 1 wherein said fixation device is a bone plate having a first screw receiving socket element at a distal end of said assembly and configured with a screw shank passage and a screw head seat for attachment to bone with the aid of a bone fixation screw, an elongate arm extending proximally from said first socket element and having an elongate through slot therealong, a second screw receiving socket element including said through passage containing said bushing and said cam means and slidably received over said arm with said socket bore aligned over said slot for receiving the shank of a fixation screw therethrough for attachment to bone, said bushing seat including portions of said through slot whereby said second socket element is clamped to said arm when said bushing is pressed downwardly into said seat by said cam means.

* * * * *

UNITED STATES PATENT AND TRADEMARK OFFICE
CERTIFICATE OF CORRECTION

PATENT NO. : 6,979,334 B2 Page 1 of 1
DATED : December 27, 2005
INVENTOR(S) : Brian E. Dalton It is certified that error appears in the above-identified patent and that said Letters Patent is hereby corrected as shown below:

<u>Title page,</u>
Item [75], Inventor, should read -- Brian E. Dalton --.

<u>Column 7,</u>
Line 55, replace "cam means disposed on and integral with said bushing." with
-- (d) cam means disposed on and integral with said bushing. --.

Signed and Sealed this

Fourteenth Day of February, 2006

JON W. DUDAS
*Director of the United States Patent and Trademark Office*